United States Patent
Gavas et al.

(10) Patent No.: US 11,141,061 B2
(45) Date of Patent: Oct. 12, 2021

(54) COGNITIVE LOAD ESTIMATION BASED ON PUPIL DILATION

(71) Applicant: Tata Consultancy Services Limited, Mumbai (IN)

(72) Inventors: Rahul Dasharath Gavas, Kolkata (IN); Debatri Chatterjee, Kolkata (IN); Aniruddha Sinha, Kolkata (IN)

(73) Assignee: Tata Consultancy Services Limited, Mumbai (IN)

(*) Notice: Subject to any disclaimer, the term of this patent is extended or adjusted under 35 U.S.C. 154(b) by 398 days.

(21) Appl. No.: 16/150,955

(22) Filed: Oct. 3, 2018

(65) Prior Publication Data
US 2019/0099075 A1  Apr. 4, 2019

(30) Foreign Application Priority Data
Oct. 3, 2017  (IN) ............................. 201721035054

(51) Int. Cl.
*A61B 5/16* (2006.01)
*A61B 3/11* (2006.01)
(Continued)

(52) U.S. Cl.
CPC .............. *A61B 3/112* (2013.01); *A61B 3/113* (2013.01); *A61B 5/163* (2017.08); *A61B 5/165* (2013.01);
(Continued)

(58) Field of Classification Search
CPC ......... A61B 5/163; A61B 3/113; A61B 5/165; A61B 5/168; A61B 5/7257; A61B 5/4088; G06F 3/013
See application file for complete search history.

(56) References Cited

U.S. PATENT DOCUMENTS

| 6,090,051 A | * | 7/2000 | Marshall ................ A61B 5/163 |
| | | | 600/558 |
| 7,344,251 B2 | | 3/2008 | Marshall |
| | | | (Continued) |

FOREIGN PATENT DOCUMENTS

WO   WO-2014/146168    9/2014

OTHER PUBLICATIONS

Stone, B. et al. (Aug. 2017). "Pupil Size and Mental Load," located at <http://www.psychology.adelaide.edu.au/cognition/aml/aml1/stone_aml1.pdf>. (6 pages).
(Continued)

*Primary Examiner* — Daniel L Cerioni
(74) *Attorney, Agent, or Firm* — Finnegan, Henderson, Farabow, Garrett & Dunner LLP (57) ABSTRACT

Traditional cognitive load estimation techniques rely on raw pupil size alone which is often prone to confound with changes in illumination, errors associated with sensor devices and irregular oscillations of pupil under constant light conditions. Estimation of cognitive load finds application in many domains including optimum work allocation, assessing a work environment and medical diagnosis. The present disclosure employs frequency domain analysis of pupil size variations to estimate load imposed by a cognitive task. A cognitive load metric based on power and frequency relations at mean frequency of the variation in pupil size addresses cognitive load estimation based on pupil dilation, wherein the pupil dilation is captured by employing low cost non-intrusive nearables.

7 Claims, 10 Drawing Sheets

(51) Int. Cl.
*G06F 3/01* (2006.01)
*A61B 3/113* (2006.01)
*A61B 5/00* (2006.01)

(52) U.S. Cl.
CPC ............ *A61B 5/168* (2013.01); *A61B 5/7257* (2013.01); *G06F 3/013* (2013.01); *A61B 5/161* (2013.01); *A61B 5/4088* (2013.01); *A61B 5/725* (2013.01); *A61B 5/7264* (2013.01)

(56) References Cited

U.S. PATENT DOCUMENTS

| 2015/0326570 | A1* | 11/2015 | Publicover | G06F 3/017 |
| | | | | 726/4 |
| 2016/0128593 | A1* | 5/2016 | Sinharay | A61B 5/7221 |
| | | | | 600/544 |
| 2016/0345060 | A1* | 11/2016 | Marci | A61B 3/113 |
| 2017/0098385 | A1 | 4/2017 | Martucci et al. | |
| 2017/0293356 | A1* | 10/2017 | Khaderi | G06F 3/147 |
| 2019/0216392 | A1* | 7/2019 | Bower | A61B 5/0533 |

OTHER PUBLICATIONS

Nuamah, J.K. et al. "Electroencephalography (EEG) Classification of Cognitive Tasks Based on Task Engagement Index," *2017 IEEE Conference on Cognitive and Computational Aspects of Situation Management (CogSIMA)*, Mar. 27-31, 2017, Savannah, GA; 6 pages.

* cited by examiner

COGNITIVE LOAD ESTIMATION BASED ON PUPIL DILATION

PRIORITY CLAIM

This U.S. patent application claims priority under 35 U.S.C. § 119 to: Indian Patent Application No. 201721035054, filed on 3 Oct. 2017. The entire contents of the aforementioned application are incorporated herein by reference.

TECHNICAL FIELD

The disclosure herein generally relates to cognitive load estimation, and particularly to cognitive load estimation based on pupil dilation.

BACKGROUND

Cognitive load corresponds to the amount of working memory demanded while performing a certain task. Estimation of cognitive load is crucial to many domains pertaining to optimum work allocation, assessing a work environment, medical diagnosis, and the like. Various physiological sensing like Electroencephalogram (EEG), Galvanic Skin Response (GSR), Electrocardiogram (ECG), skin temperature, Electromyogram (EMG), Photoplethesmography (PPG), etc. have been used to determine cognitive load in the art. These techniques require subjects to wear physiological sensors which may be uncomfortable/unacceptable in certain scenarios. However, with the advent of nearable eye trackers, nowadays, it is possible to remotely assess cognitive load imposed on a subject. Moreover, these devices are easy to use as they do not impose additional overhead experienced due to wearable sensors like head mounted eye trackers. Eye movements and pupil size variations render valuable information pertaining to the psychological states of the subjects. Normally pupils dilate in the absence of light in order to allow more light to pass into the eye. However, there are other instances resulting in pupil dilation like challenging cognitive task (termed as task evoked pupillary response (TEPR)), emotional states, medication, etc. These changes are involuntary actions and most of the time it happens unconsciously. Thus, the same pupil dilation might represent different conditions and the exact meaning depends largely on the situation. Estimating cognitive load based on pupil dilation is therefore a challenge.

SUMMARY

Embodiments of the present disclosure present technological improvements as solutions to one or more of the above-mentioned technical problems recognized by the inventors in conventional systems.

In an aspect, there is provided a processor implemented method comprising: capturing a cognitive task evoked pupillary response in the form of raw pupil size data associated with a subject, wherein the capturing is based on remote eye tracking; pre-processing the captured raw pupil size data to obtain filtered data; and performing frequency domain analysis on the filtered data to obtain cognitive load L(t) by: computing mean frequency $f(\omega)$ of the filtered data based on (i) number of frequency bins n, (ii) frequency band $\omega_i$ of each of the frequency bins i, and (iii) frequency $f_{\omega_i}$ and energy density $I_{\omega_i}$ associated with each of the frequency bins; and computing cognitive load L(t) based on the mean frequency $f(\omega)$ and power $p(\omega)$ corresponding to the mean frequency $f(\omega)$.

In another aspect, there is provided a system comprising: one or more data storage devices operatively coupled to the one or more processors and configured to store instructions configured for execution by the one or more processors to: capture a cognitive task evoked pupillary response in the form of raw pupil size data associated with a subject, wherein the capture is based on remote eye tracking; pre-process the captured raw pupil size data to obtain filtered data; and perform frequency domain analysis on the filtered data to obtain cognitive load L(t) by: computing mean frequency $f(\omega)$ of the filtered data based on (i) number of frequency bins n, (ii) frequency band $\omega_i$ of each of the frequency bins i, and (iii) frequency $f_{\omega_i}$ and energy density $I_{\omega_i}$ associated with each of the frequency bins; and computing cognitive load L(t) based on the mean frequency $f(\omega)$ and power $p(\omega)$ corresponding to the mean frequency $f(\omega)$.

In yet another aspect, there is provided a computer program product comprising a non-transitory computer readable medium having a computer readable program embodied therein, wherein the computer readable program, when executed on a computing device, causes the computing device to: capture a cognitive task evoked pupillary response in the form of raw pupil size data associated with a subject, wherein the capture is based on remote eye tracking; pre-process the captured raw pupil size data to obtain filtered data; and perform frequency domain analysis on the filtered data to obtain cognitive load L(t) by: computing mean frequency $f(\omega)$ of the filtered data based on (i) number of frequency bins n, (ii) frequency band $\omega_i$ of each of the frequency bins i, and (iii) frequency $f_{\omega_i}$ and energy density $I_{\omega_i}$ associated with each of the frequency bins; and computing cognitive load L(t) based on the mean frequency $f(\omega)$ and power $p(\omega)$ corresponding to the mean frequency $f(\omega)$.

In an embodiment of the present disclosure, the one or more hardware processors are further configured to perform pre-processing by interpolating missed data in the captured raw pupil size data to obtain adjusted raw pupil data based on previous and subsequent data; and low pass filtering of the adjusted raw pupil data to eliminate noise and obtaining filtered data.

In an embodiment of the present disclosure, the one or more hardware processors are further configured to perform frequency domain analysis on the filtered data comprises segmenting the filtered data to obtain baseline and trial portions based on time stamps extracted from metadata associated with the raw pupil size data.

In an embodiment of the present disclosure, the one or more hardware processors are further configured to compute mean frequency $f(\omega)$ of the filtered data by performing short-time Fourier transform (s-transform) to obtain frequency $f_{\omega_i}$ and power $p_{\omega_i}$ associated with each of the frequency bins.

It is to be understood that both the foregoing general description and the following detailed description are exemplary and explanatory only and are not restrictive of the embodiments of the present disclosure, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Cognitive load or mental workload is characterized by the amount of memory resources utilized to ascertain a task. As per the cognitive load theory, cognitive load can be broadly classified into three major classes, viz., intrinsic load, extraneous load and germane load. Intrinsic load is experienced due to the complexity of the task itself. For instance, adding 2 digit numbers is comparatively difficult than adding single digit numbers. Extraneous load occurs owing to the presentation of the information in the task; for instance, presenting data graphically over a tabulated format. The former induces lower extraneous load over the latter. Germane load occurs during comprehending and processing of new information. Most of the existing researches use raw pupil size as an indicator of mental workload and they do not use any specific metric which can be used to differentiate between various levels of cognitive load. The present disclosure is directed towards intrinsic cognitive load and for all purposes, the expression "cognitive load" referred hereinafter in the present disclosure refers to intrinsic cognitive load.

Traditional techniques of assessing cognitive load involved analyzing performance measures like total score or time taken to analyze the cognitive load imposed during a task. However, this method involves customizing the performance measures to the task as the tasks differ often. Also, this method lacks continuous monitoring as the performance score is obtained after a certain interval or after the completion of the task. Another method employed in the art is a questionnaire based approach which gives subjective measures of the task difficulty experienced by the user and is generally done after the task completion. This method is highly biased and solely depends on the subject's perception of work load.

Physiological sensing provides relatively better estimation in the art. It renders real time monitoring of load imposed on the subject without their knowledge. Perceptual-motor changes during a task may be measured using sensors and by inference the perceptual-motor changes are attributed to cognitive performance of the subject. High resolution sensors are efficient in terms of accuracy, however, their increased cost and complexity has created a surge for affordable and easy to use devices. However, such affordable devices are basically low resolution ones and are prone to noise inherent due to sensor mechanics involved.

The present disclosure is directed towards employing low cost non-intrusive wearables that are traditionally considered inefficient in facilitating cognitive load estimation. Changes in screen illumination, ethnic differences among the subjects, operating distance from the screen, data loss due to blinks and other related measurement noise form key factors that affect efficiency of cognitive load estimation. Unobtrusive eye tracking is advantageous for scenarios like evaluation of distraction, mental effort, anxiety etc. Subjects may get disturbed while wearing the eye trackers mounted on head which may lead to distortion of results. Hence, in accordance with the present disclosure, non-intrusive wearables in the form of nearables such as low cost, infrared-based eye trackers are employed to capture raw pupil size data to quantify the cognitive load based on dilating nature of the pupil. Particularly, the present disclosure distinguishes and quantifies the intrinsic cognitive load into two classes— low and high loads using the dilating nature of the pupil. In accordance with the present disclosure, a metric is provided to estimate cognitive load based on the pupil dilation and validated based on nature of visual field area and the percentage change in pupil diameter and also with the intelligence level of the participants, thereby eliminating the inherent inefficiency traditionally associated with low cost nearables.

Referring now to the drawings, and more particularly to FIGS. 1 through 10, where similar reference characters denote corresponding features consistently throughout the figures, there are shown preferred embodiments and these embodiments are described in the context of the following exemplary system and method.

Figure 1:
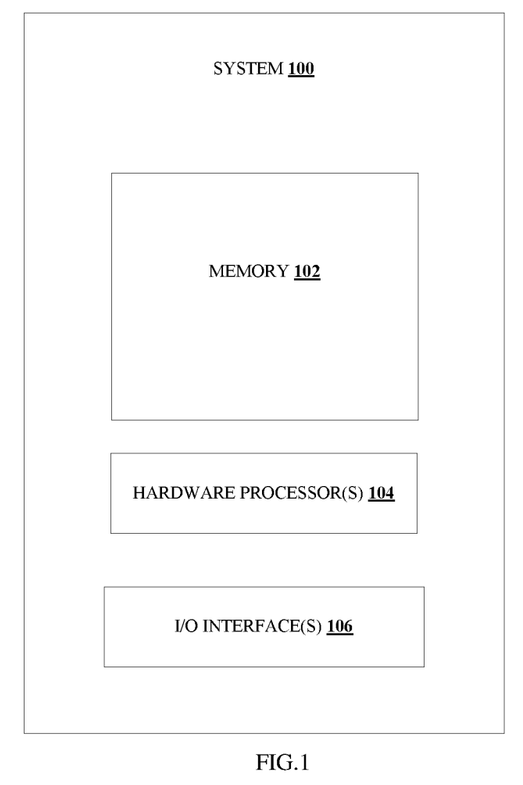
FIG. 1 illustrates an exemplary block diagram of a system for cognitive load estimation based on pupil dilation, in accordance with an embodiment of the present disclosure.

FIG. 1 illustrates an exemplary block diagram of a system 100 for cognitive load estimation based on pupil dilation, in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

In an embodiment, the system 100 comprises one or more data storage devices or memory 102 operatively coupled to the one or more processors 104 and is configured to store instructions configured for execution of steps of the method 200 by the one or more processors 104.

Figure 2:
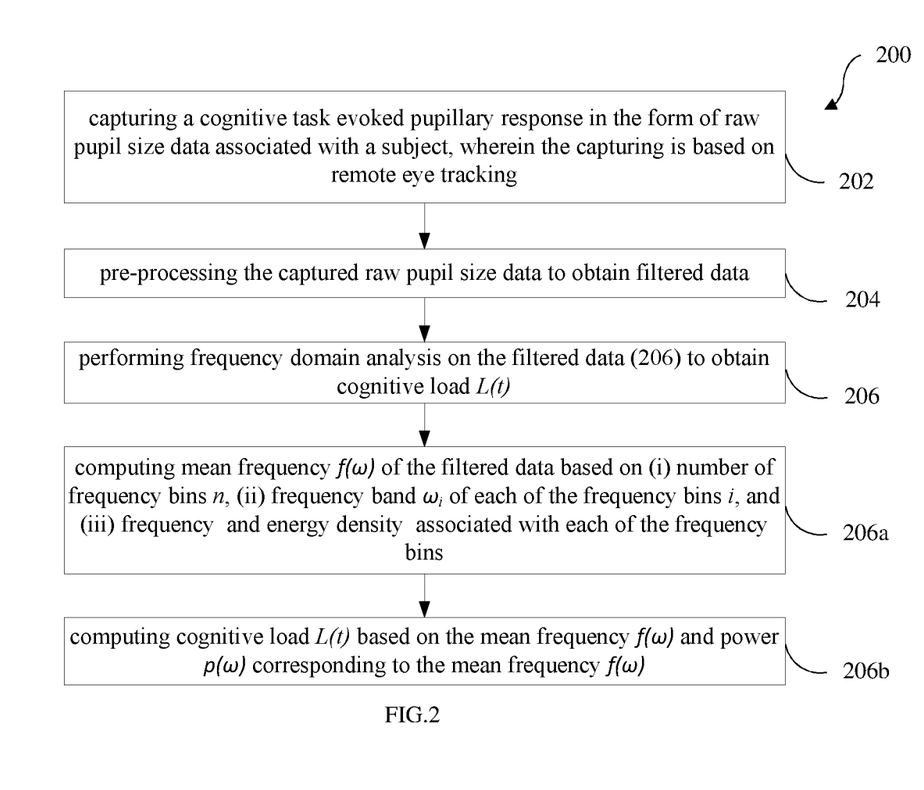
FIG. 2 is an exemplary flow diagram illustrating a computer implemented method for cognitive load estimation based on pupil dilation, in accordance with an embodiment of the present disclosure.

FIG. 2 is an exemplary flow diagram illustrating a computer implemented method for cognitive load estimation based on pupil dilation, in accordance with an embodiment of the present disclosure. The steps of the method 200 will now be explained in detail with reference to the components of the system 100 of FIG. 1. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

In accordance with an embodiment of the present disclosure, the one or more processors 104 are configured to capture, at step 202, a cognitive task evoked pupillary response in the form of raw pupil size data associated with a subject, wherein the capturing is based on remote eye tracking. In an embodiment, EyeTribe™ eye tracker may be used. Good calibration may be ensured to analyze the impact of eye motion under cognitive load since deviation from target gaze location is critical to the analyses. The raw pupil size data obtained by remote eye tracking may contain some missing values due to eye blinks or some abrupt values of pupil size due to hardware glitches. Remote eye tracker like EyeTribe™ returns a zero value during the blink interval.

Accordingly, in accordance with an embodiment of the present disclosure, the one or more processors 104 are configured to pre-process, at step 204, the captured raw pupil size data to obtain filtered data. In an embodiment the missing portions in the captured raw pupil size data may be interpolated based on previous and consequent data points to obtain adjusted raw pupil data, wherein the adjusted raw pupil data accounts for the missing portions to ensure availability of continuous data. Pupil responses during cognitive activities mainly occur below 4 Hz above which the signal is mainly due to measurement noise. Accordingly, the pre-processing at step 204 may include low pass filtering of the adjusted raw pupil data by a low pass filter having a cutoff frequency of 4 Hz to eliminate noise and obtain filtered data.

In accordance with the present disclosure, the one or more processors 104 are configured to perform frequency domain analysis, at step 206, on the filtered data to obtain cognitive load L(t). The step of performing frequency domain analysis on the filtered data comprises segmenting the filtered data to obtain baseline and trial portions based on time stamps extracted from metadata associated with the raw pupil size data. The baseline portion is illustrated in an exemplary embodiment depicted in FIG. 3 and the associated description. The trial portions follow the marked base line portions. The estimated cognitive load is a function of a sequence of load pulses with varying magnitudes. The total cognitive load imparted for a given trial portion is thereby a combination of all the load pulses.

In accordance with the present disclosure, short-time Fourier transform (s-transform) is performed to obtain frequency $f_{\omega_i}$ and power $p_{\omega_i}$ for each frequency bin associated with the filtered data. In accordance with an embodiment, the one or more processors are configured to compute mean frequency $f(\omega)$ of the filtered data, at step 206a, based on (i) number of frequency bins n, (ii) frequency band $\omega_i$ of each of the frequency bins i, and (iii) frequency $f_{\omega_i}$ and energy density $I_{\omega_i}$ associated with each of the frequency bins. The mean frequency $f(\omega)$ of the filtered data, in accordance with the present disclosure may be represented as given below.

$$f(\omega) = \frac{\sum_{i=0}^{n-1} I_{\omega_i} f_{\omega_i}}{\sum_{i=0}^{n-1} I_{\omega_i}} \qquad (1)$$

In accordance with an embodiment, the one or more processors are configured to compute cognitive load L(t), at step 206b, based on the mean frequency $f(\omega)$ and power $p(\omega)$ corresponding to the mean frequency $f(\omega)$. Accordingly, the cognitive load L(t) may be represented as given below.

$$L(t) = p(\omega) * f(\omega) \qquad \rightarrow (2)$$

EXPERIMENTAL DATA

A mental addition task was used and developed using Matlab to impart low and high cognitive loads on subjects. In the low load task, single digit numbers from 0-5 were used, whereas for the high load task, numbers in the range of 6-19 were selected. Numbers such as 10, 11 and 15 were excluded since they are relatively easier to add with other numbers. In all, 10 numbers for the low load and 10 numbers for the high load were selected.

Figure 3:
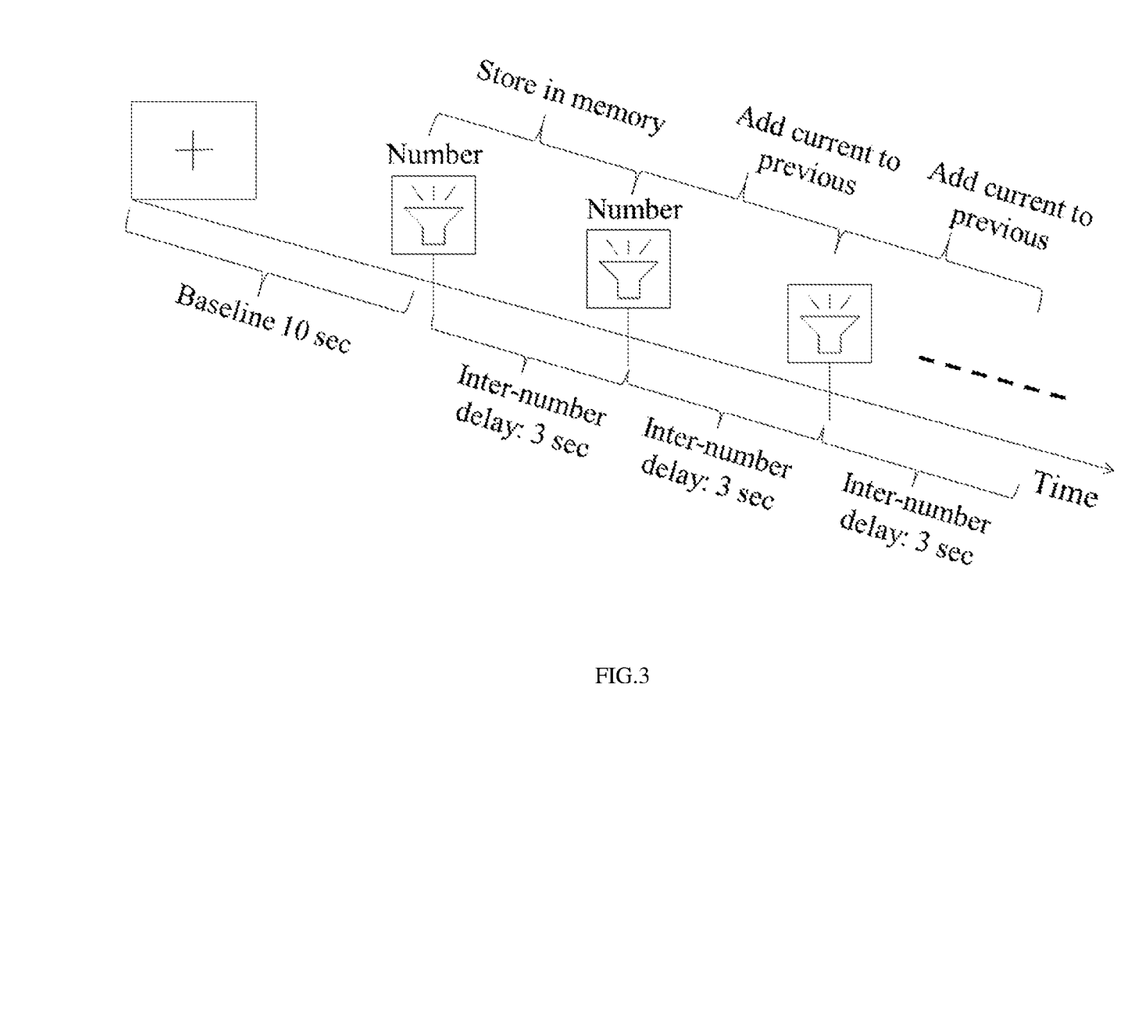
FIG. 3 illustrates stimulus and cognitive tasks assigned to a subject in an exemplary setup in accordance with an embodiment of the present disclosure.
Figure 4:
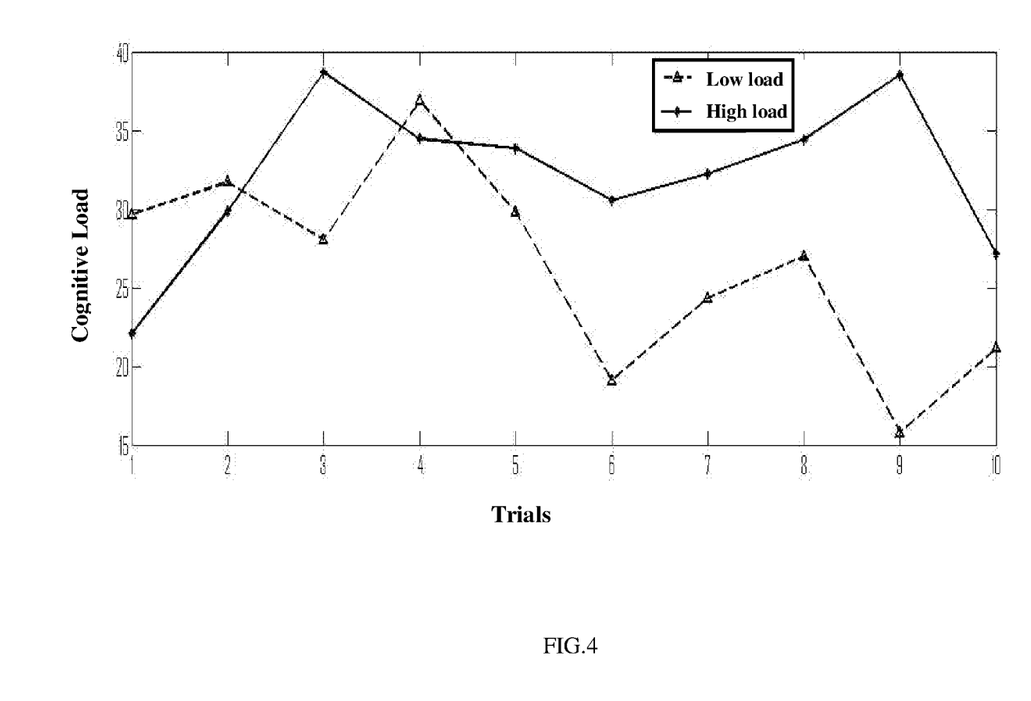
FIG. 4 illustrates variations of estimated cognitive load values, in accordance with an embodiment of the present disclosure, for a participant.

Fifteen participants (7 females, 8 males, mean age: 28±8 years) participated in the study. Necessary consents and clearance were obtained from the participants. It was ensured that the participants have similar cultural and educational backgrounds. All the participants had normal or corrected to normal vision with spectacles and all were right handed. At the beginning, the task and the procedure were explained to them. In order to ensure that the participants followed the tasks properly, a demo version of the task was performed before starting the actual data capture. EyeTribe™ eye tracker was used for the study. An initial calibration was done using the Software Development Kit (SDK) based calibration procedure to obtain a calibration score of 5, which is indicative of good calibration. The sampling frequency of the eye tracker was 30 Hz. A chin rest was used in order to ensure minimal head movements and kept at a distance of 60 cm away from the participant. The experiment was carried out in a closed quite room with constant lighting conditions. The participants wore a headphone to listen to the stimulus. A 10 second baseline section preceded the task during which the participants were asked to focus on a fixation cross in white background that was displayed in the midst of the computer screen. The fixation cross was used so that the participants are forced to keep their eyes open while calculating mentally. A series of numbers is played one after another with an interval of 3 seconds and the participants were instructed to add them mentally. FIG. 3 illustrates stimulus and cognitive tasks assigned to a subject in an exemplary setup in accordance with an embodiment of the present disclosure. The tone of the numbers is generated through a computer program so that same sound characteristics are maintained across all trial portions. Timestamps at appropriate locations were logged for further analysis. For 7 out of 15 participants, the low load task was administered first followed by the high load task. For rest of the participants, reverse order was followed in order to avoid any bias related effects owing to the sequence of the task. The eye tracker returned a zero value during blink intervals that lasted for almost 70-300 ms. These blink portions were interpolated and low pass filtering was performed to eliminate noise and obtain filtered data. The cognitive load imposed on a participant were computed using equation (2) above. FIG. 4 illustrates variations of estimated cognitive load values, in accordance with an embodiment of the present disclosure, for a participant. As the trial proceeds, the total load imparted on the participant also increases and is evident from FIG. 4.

Figure 5:
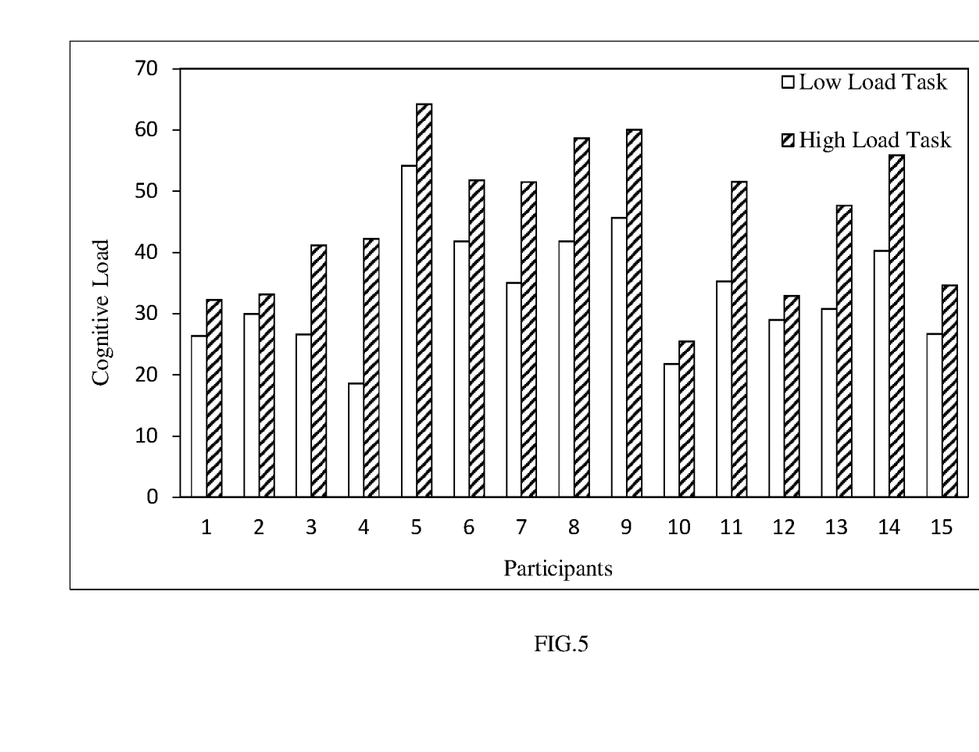
FIG. 5 illustrates estimated cognitive load values, in accordance with an embodiment of the present disclosure, averaged over all trials.

Similar trend is followed for the rest of the participants. The cognitive load is estimated per session and averaged across both the low and the high load tasks and is illustrated in FIG. 5. It is noted that the difference between the cognitive loads corresponding to the low and high load tasks were significant for all the participants, thereby illustrating consistency of the proposed metric for cognitive load estimation.

Figure 6:
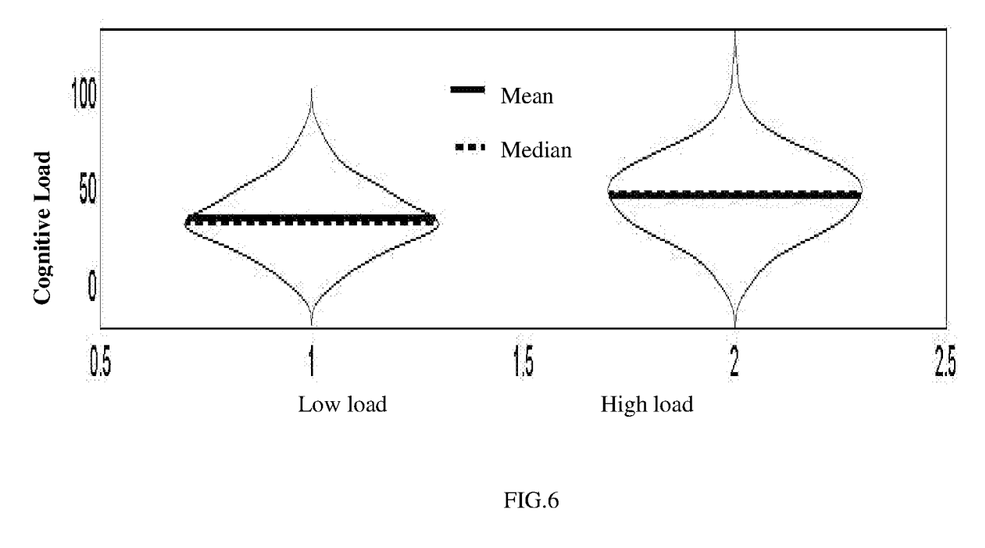
FIG. 6 illustrates the nature of the distribution of the cognitive load points computed, in accordance with an embodiment of the present disclosure, for all the participants across trials, through a violin plot.

FIG. 6 illustrates the nature of the distribution of the cognitive load points computed, in accordance with an embodiment of the present disclosure, for all the participants across trials, through a violin plot. The data points are statistically different with a p=1.34e−08.

The performance of the method of the present disclosure was further compared with existing methods namely Percentage change in pupil diameter (PCPD), perimeter-area ratio (PAR) and form factor (FF) to distinguish the two levels of cognitive load.

An obvious means of cognitive load assessment in pupillometry is by measuring the percentage change in pupil diameter (PCPD) with respect to that during the baseline portion. Generally, the PCPD increases with increase in cognitive load. Generally PCPD increases with increase in cognitive load. Accordingly, this metric was used for comparison with the method of the present disclosure.

Cognitive load may also be estimated based on the nature of visual field of the eyes during the stimulus. During the data capture phase, the eye tracker captures noisy (x,y) coordinates of the gaze on the screen. S represents a set of all captured coordinates over a period of time and the set S is represented through equation (3)

$$S = [(x_1,y_1),(x_2,y_2), \ldots ,(x_n,y_n)]^T \quad \rightarrow (3)$$

where n is the number of samples in the signal. The missing data due to blinks in the set S are adjusted with interpolation based on previous and subsequent data samples. The perimeter-area ratio (PAR), was computed to estimate the cognitive load, given by equation (4), $$PAR = \frac{\sqrt{Area}}{(0.282 \times Perimeter)} \quad (4)$$

where the constant 0.282 returns a value of 1 in case of circles, and decreases as the shape gets compact. A zero value signifies a line having zero area.

The FF method is given by equation (5), $$FF = \frac{4 \times \pi \times Area}{Perimeter^2} \quad (5)$$

Figure 7:
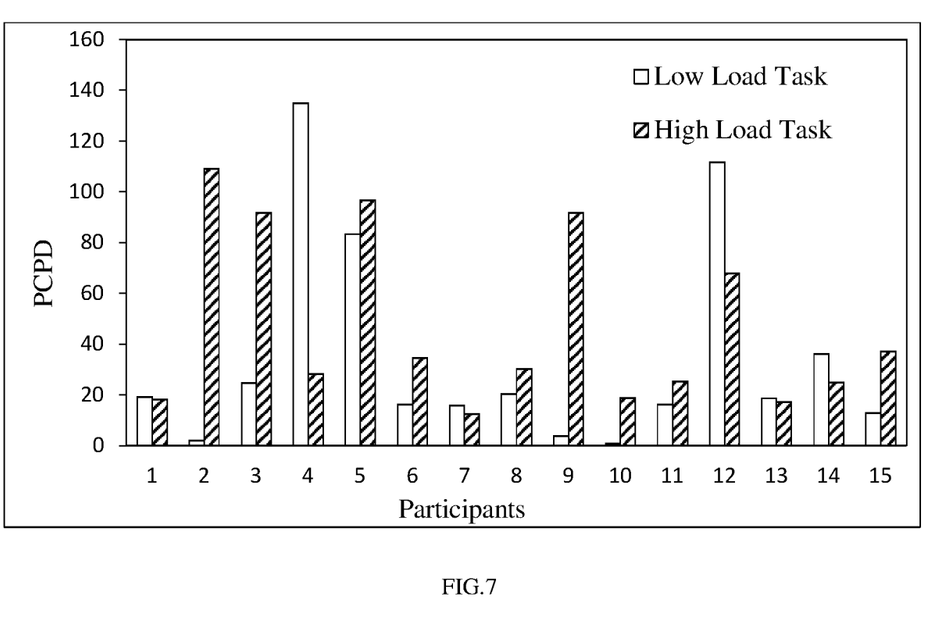
FIG. 7 illustrates the percentage change in pupil diameter (PCPD), as known in the art, averaged over all the trial portions.
Figure 8:
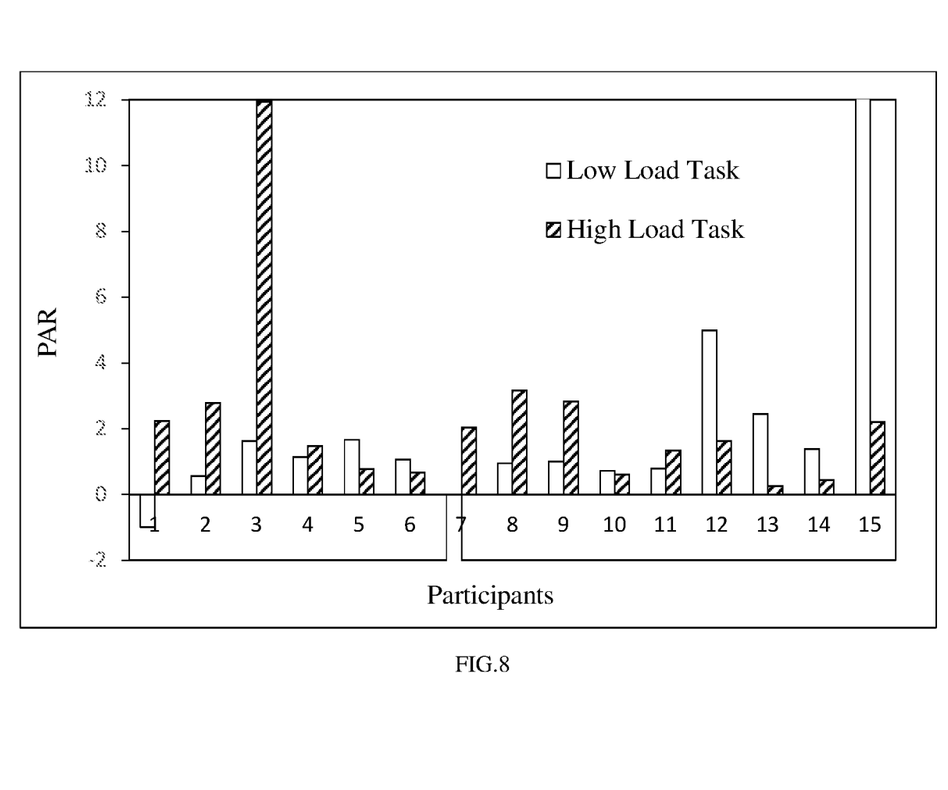
FIG. 8 illustrates the perimeter-area ratio (PAR), as known in the art, averaged over all the trial portions.
Figure 9:
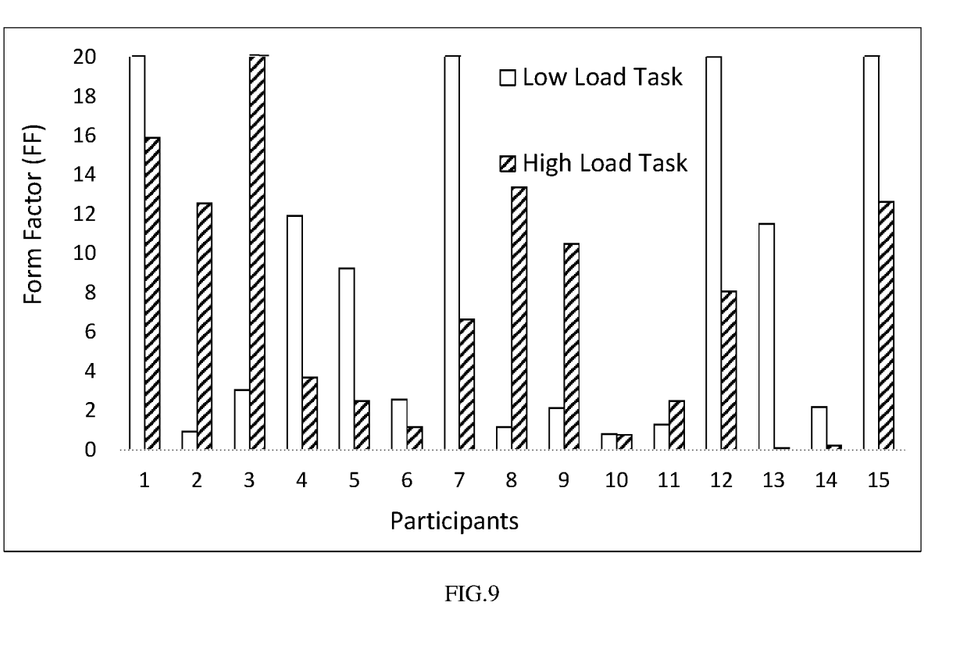
FIG. 9 illustrates the form factor (FF), as known in the art, averaged over all the trial portions.

The cognitive load values were computed for each trial portion for the low and high load tasks for each participant and the average values are reported in FIGS. 7, 8 and 9 wherein FIG. 7 illustrates the percentage change in pupil diameter (PCPD), as known in the art, averaged over all the trial portions; FIG. 8 illustrates the perimeter-area ratio (PAR), as known in the art, averaged over all the trial portions; and FIG. 9 illustrates the form factor (FF), as known in the art, averaged over all the trial portions respectively. It is evident that there is no consistent pattern for distinguishing the two levels of loads imparted on the participants. For instance, PCPD failed to distinguish the low and high levels of cognitive load for few participants namely, 4, 7, 12, 13 and 14, where reverse trends are observed. For PAR, though there is a considerable amount of separation between the two tasks, the reverse pattern is observed for participants 5, 6, 12, 13, 14 and 15. Similar results are also obtained with FF across the participants.

In order to further evaluate separation for the low and high load tasks, the discriminating index (DI) was computed per trial i, as given in equation (6), $$d_i = \begin{cases} 1, & D_{High_i} > D_{Low_i} \\ 0, & \text{otherwise} \end{cases} \quad (6)$$

where D is the estimated cognitive load metric in accordance with the present disclosure or other metrics like PCPD, PAR or FF. The time duration for both the loads is same and hence, d is computed per trial portion in each of the cases.

Next, the total discriminating index TDI is computed as given in equation (7), $$TDI = \frac{1}{N}\sum_{i=1}^{N} d_i \times 100 \qquad (7)$$

Table I below shows the TD/values for the estimated cognitive load metric in accordance with the present disclosure and the state of the art methods (averaged across the participants).

TABLE I

| Approach | Method of the present disclosure | PCPD | PAR | FF |
|---|---|---|---|---|
| Average TDI | 71.34% | 64.67% | 46.67% | 66.67% |

It is evident from the results in the table that the method of the present disclosure outperforms the existing metrics.

Figure 10:
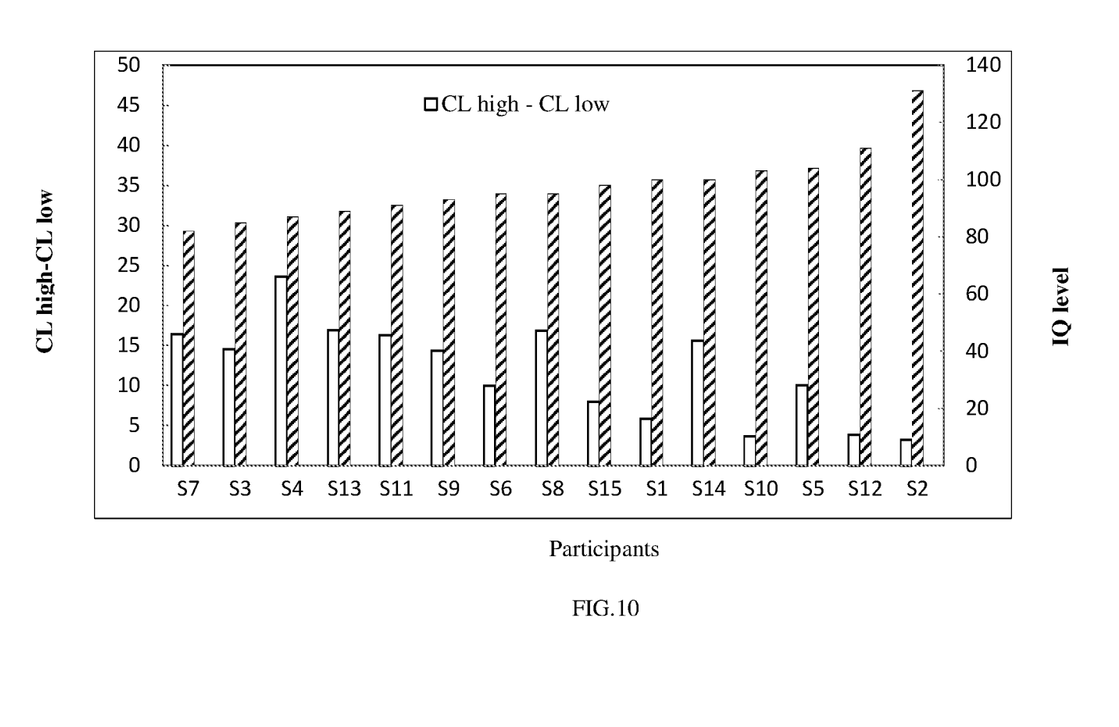
FIG. 10 illustrates the variations in estimated cognitive load (i.e. cognitive load for high load task-cognitive load for low load task) in accordance with an embodiment of the present disclosure versus IQ levels.

As part of further validation, tests were conducted to investigate the relation between the method of the present disclosure and Intelligence Quotient (IQ) of the participants. The IQ level of an individual is known to be inversely proportional to the overall cognitive load. Higher the IQ, better is the management of mental resources and hence, less is the total cognitive load. In order to check if the metric of the present disclosure is reliable enough, the total cognitive load was compared with IQ levels of the participants. As part of the experimental procedure, an online IQ test by Brainmetrix™ was taken by the participants. FIG. 10 illustrates the variations in estimated cognitive load (i.e. cognitive load for high load task-cognitive load for low load task) in accordance with an embodiment of the present disclosure versus IQ levels. For ease of analysis, the participants were sorted in increasing values of IQ. It was seen that for participants having higher IQ levels, the difference in the load imposed is less, indicating that the cognitive load for high load is relatively less. Thus, the method of the present disclosure conforms to the variations in cognitive load with IQ. This also shows the ability of the method of the present disclosure to handle subjective differences of the users under test.

Cognitive load is imposed during all the day-to-day activities and tasks that require usage of working memory and the related resources. In accordance with the present disclosure, systems and methods of the present disclosure provide a metric for the estimation of cognitive load based on the dilating nature of pupil size. A mental addition task was used with two variants—easy and difficult to induce low and high loads, respectively, on the participants. The metric is based on the mean frequency and power of dilation of the pupil size for both the low and the high load tasks. It was seen that there is substantial amount of separation achieved in both the cases and the nature of separation is consistent for all the participants. The method of the present disclosure was also compared with the state-of-the art methods that are based on the percentage change in pupil dilation (PCPD) and the visual field metrics like perimeter-area ratio (PAR) and form factor (FF). It is noted that the method of the present disclosure outperforms the rest of the approaches in distinguishing the two levels of cognitive loads. Also, there was an inverse relation observed in case of the difference in the high and low loads vs the IQ levels of the participants. This shows that the candidates with higher IQ levels feel less load during the high load tasks in conjunction to the low load task.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method (200) comprising:
   capturing a cognitive task evoked pupillary response in the form of raw pupil size data associated with a subject to quantify cognitive load based on dilating nature of pupil, wherein the capturing is based on remote eye tracking (202);
   distinguishing and quantifying the cognitive load into two classes namely low and high loads using the dilating nature of the pupil;
   providing a metric to estimate the cognitive load based on the pupil dilation;
   validating the cognitive load based on nature of visual field area and percentage change in pupil diameter and intelligence level of the subject;
   pre-processing the captured raw pupil size data to obtain filtered data (204); and
   performing frequency domain analysis on the filtered data (206) to obtain cognitive load L(t) by:
   computing mean frequency $f(\omega)$ of the filtered data based on (i) number of frequency bins n, (ii) frequency band $\omega_i$ of each of the frequency bins i, and (iii) frequency $f_{\omega_i}$ and energy density $I_{\omega_i}$ associated with each of the frequency bins (206a); and
   computing the cognitive load L(t) based on the mean frequency $f(\omega)$ and power $p(\omega)$ corresponding to the mean frequency $f(\omega)$ (206b)
   wherein the step of performing frequency domain analysis on the filtered data comprises segmenting the filtered data to obtain baseline and trial portions based on time stamps extracted from metadata associated with the raw pupil size data, and
   wherein computing cognitive load L(t) is a function of a sequence of load pulses with varying magnitudes and a total cognitive load imparted for a given trial portion is a combination of all the load pulses.

2. The processor implemented method of claim 1, wherein the step of pre-processing comprises:
   interpolating missed data in the captured raw pupil size data to obtain adjusted raw pupil data based on previous and subsequent data; and
   low pass filtering of the adjusted raw pupil data to eliminate noise and obtaining filtered data.

3. The processor implemented method of claim 1, wherein the step of computing mean frequency $f(\omega)$ of the filtered data comprises performing short-time Fourier transform (s-transform) to obtain frequency the $f_{\omega_i}$ and energy density $I_{\omega_i}$ associated with each of the frequency bins.

4. A system (100) comprising:
   one or more data storage devices (102) operatively coupled to one or more hardware processors (104) and configured to store instructions configured for execution by the one or more hardware processors to:
   capture a cognitive task evoked pupillary response in the form of raw pupil size data associated with a subject to quantify cognitive load based on dilating nature of pupil, wherein the capture is based on remote eye tracking;
   distinguishing and quantifying the cognitive load into two classes namely low and high loads using the dilating nature of the pupil;
   providing a metric to estimate the cognitive load based on the pupil dilation;
   validating the cognitive load based on nature of visual field area and percentage change in pupil diameter and intelligence level of the subject;
   pre-process the captured raw pupil size data to obtain filtered data; and
   perform frequency domain analysis on the filtered data to obtain cognitive load L(t) by:
   computing mean frequency $f(\omega)$ of the filtered data based on (i) number of frequency bins n, (ii) frequency band $\omega_i$ of each of the frequency bins i, and (iii) frequency $f_{\omega_i}$ and energy density $I_{\omega_i}$ associated with each of the frequency bins; and
   computing cognitive load L(t) based on the mean frequency $f(\omega)$ and power $p(\omega)$ corresponding to the mean frequency $f(\omega)$
   wherein the step of performing frequency domain analysis on the filtered data comprises segmenting the filtered data to obtain baseline and trial portions based on time stamps extracted from metadata associated with the raw pupil size data, and
   wherein computing cognitive load L(t) is a function of a sequence of load pulses with varying magnitudes and a total cognitive load imparted for a given trial portion is a combination of all the load pulses.

5. The system of claim 4, wherein the one or more hardware processors are further configured to pre-process the captured raw pupil size data by:
   interpolating missed data in the captured raw pupil size data to obtain adjusted raw pupil data based on previous and subsequent data; and
   low pass filtering of the adjusted raw pupil data to eliminate noise and obtaining filtered data.

6. The system of claim 4, wherein the one or more hardware processors are further configured to compute mean frequency $f(\omega)$ of the filtered data by performing short-time Fourier transform (s-transform) to obtain frequency $f_{\omega_i}$ and the energy density $I_{\omega_i}$ associated with each of the frequency bins.

7. A computer program product comprising a non-transitory computer readable medium having a computer readable program embodied therein, wherein the computer readable program, when executed on a computing device, causes the computing device to:
   capture a cognitive task evoked pupillary response in the form of raw pupil size data associated with a subject to quantify cognitive load based on dilating nature of pupil, wherein the capturing is based on remote eye tracking;

distinguishing and quantifying the cognitive load into two classes namely low and high loads using the dilating nature of the pupil;

providing a metric to estimate the cognitive load based on the pupil dilation;

validating the cognitive load based on nature of visual field area and percentage change in pupil diameter and intelligence level of the subject;

pre-process the captured raw pupil size data to obtain filtered data; and perform frequency domain analysis on the filtered data to obtain cognitive load L(t) by:

computing mean frequency $f(\omega)$ of the filtered data based on (i) number of frequency bins n, (ii) frequency band $\omega_i$ of each of the frequency bins i, and (iii) frequency $f_{\omega_i}$ and energy density $I_{\omega_i}$ associated with each of the frequency bins; and computing cognitive load L(t) based on the mean frequency $f(\omega)$ and power $p(\omega)$ corresponding to the mean frequency $f(\omega)$ wherein the step of performing frequency domain analysis on the filtered data comprises segmenting the filtered data to obtain baseline and trial portions based on time stamps extracted from metadata associated with the raw pupil size data, and wherein computing cognitive load L(t) is a function of a sequence of load pulses with varying magnitudes and a total cognitive load imparted for a given trial portion is a combination of all the load pulses.

\* \* \* \* \*